(12) United States Patent
Pimentel et al.

(10) Patent No.: US 10,736,343 B2
(45) Date of Patent: *Aug. 11, 2020

(54) ANTIMICROBIAL FORMULATIONS WITH PELARGONIC ACID

(71) Applicant: ANITOX CORPORATION, Lawrenceville, GA (US)

(72) Inventors: Julio Pimentel, Buford, GA (US); Kurt Richardson, Maysville, GA (US)

(73) Assignee: ANITOX CORPORATION, Lawrenceville, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/347,626

(22) PCT Filed: Oct. 8, 2012

(86) PCT No.: PCT/US2012/059169
§ 371 (c)(1),
(2) Date: Mar. 26, 2014

(87) PCT Pub. No.: WO2013/059012
PCT Pub. Date: Apr. 25, 2013

(65) Prior Publication Data
US 2015/0031762 A1    Jan. 29, 2015

Related U.S. Application Data

(60) Provisional application No. 61/549,661, filed on Oct. 20, 2011.

(51) Int. Cl.
*A23L 3/3463* (2006.01)
*A01N 35/02* (2006.01)
*A01N 37/02* (2006.01)
*A23K 20/158* (2016.01)
*A23K 50/75* (2016.01)
*A23K 20/105* (2016.01)
*A61L 2/16* (2006.01)
*C02F 1/50* (2006.01)

(52) U.S. Cl.
CPC .......... *A23L 3/34635* (2013.01); *A01N 35/02* (2013.01); *A01N 37/02* (2013.01); *A23K 20/105* (2016.05); *A23K 20/158* (2016.05); *A23K 50/75* (2016.05); *A61L 2/16* (2013.01); *A23V 2002/00* (2013.01); *C02F 1/50* (2013.01)

(58) Field of Classification Search
CPC ................. A01N 35/02; A01N 37/02
See application file for complete search history.

(56) References Cited

U.S. PATENT DOCUMENTS

| | | |
|---|---|---|
| 5,093,124 A | 3/1992 | Kulenkampff |
| 5,342,630 A | 8/1994 | Jones |
| 5,366,995 A | 11/1994 | Savage et al. |
| 5,547,987 A | 8/1996 | Bland et al. |
| 5,587,358 A | 12/1996 | Sukigara et al. |
| 5,591,467 A | 1/1997 | Bland et al. |
| 5,663,152 A | 9/1997 | Hayano et al. |
| 5,673,468 A | 10/1997 | Pumpe |
| 5,698,599 A | 12/1997 | Subbiah |
| 5,776,919 A | 7/1998 | Sukigara et al. |
| 5,849,956 A | 12/1998 | Koga et al. |
| 5,911,915 A | 6/1999 | Fonsny et al. |
| 5,939,050 A | 8/1999 | Iyer et al. |
| 6,103,768 A | 8/2000 | Savage et al. |
| 6,121,224 A | 9/2000 | Fonsny et al. |
| 6,136,856 A | 10/2000 | Savage et al. |
| 6,201,026 B1 | 3/2001 | Hammond et al. |
| 6,323,171 B1 | 11/2001 | Fonsny et al. |
| 6,468,953 B1 | 10/2002 | Hitchems et al. |
| 6,387,866 B1 | 11/2002 | Mondin et al. |
| 6,475,976 B1 | 11/2002 | Mahieu et al. |
| 6,479,044 B1 | 11/2002 | Mahieu et al. |
| 6,479,454 B1 | 11/2002 | Smith et al. |
| 6,566,312 B2 | 5/2003 | Bettiol |
| 6,569,261 B1 | 5/2003 | Aubay et al. |
| 6,596,681 B1 | 7/2003 | Mahieu et al. |
| 6,596,763 B1 | 7/2003 | Thormar et al. |
| 6,638,978 B1 | 10/2003 | Kabara |
| 6,750,256 B1 | 6/2004 | Crandall, Jr. et al. |
| 6,855,669 B2 | 2/2005 | Knowles et al. |
| 6,960,350 B2 | 11/2005 | Hanada et al. |
| RE39,543 E | 4/2007 | Emerson et al. |
| 7,638,114 B1* | 12/2009 | Schur .............................. 424/45 |
| 9,290,448 B2 | 3/2016 | Li et al. |

(Continued)

FOREIGN PATENT DOCUMENTS

| | | |
|---|---|---|
| CN | 1268874 A | 10/2000 |
| DE | 161131 A1 | 2/1985 |

(Continued)

OTHER PUBLICATIONS

Virginia Department of Health Division of Health Hazards Control—Acetic Acid http://www.vdh.virginia.gov/epidemiology/DEE/PublicHealthToxicology/documents/pdf/aceticacid.PDF.*
Transportation Service (TIS) http://www.tis-gdv.de/tis_e/ware/gewuerze/zimt/zimt.htm.*
Power, E.G.M., "Aldehydes as Biocides" in Progress in Medicinal Chemistry—vol. 34, edited by G.P. Ellis and D.K. Luscombe © 1997, Elsevier Science BV.*
Swedish Government—SOU1997:132; Chapter 1-4, Antimicrobial Feed Additives.*
2005, Dilantha Fernando, W.G., R. Ramaranthnam, A. Krihnamoorthy and S. Savchuck. Identification and use of potential organic antifungal volatiles in biocontrol. 50i/ Biology ond Biochemistry. 2005 v.37, 955-964.
1991, Hamilton-Kemp, et. al, (1. Agric. Food Chem. 1991, v. 39, No. 5, 952-956.

(Continued)

*Primary Examiner* — San Ming R Hui
(74) *Attorney, Agent, or Firm* — Thompson Coburn LLP; Steven M. Ritchey

(57) ABSTRACT

An antimicrobial composition for extending the shelf-life of water, feed or feed ingredients, comprising: water, a mixture of CrC18 organic acids, a mixture of CrC24 aldehydes, 5-25 wt. % pelargonic acid, and 5-30 wt. % trans-2-hexenal.

4 Claims, No Drawings

(56) References Cited

U.S. PATENT DOCUMENTS

| | | |
|---|---|---|
| 2002/0009527 A1 | 1/2002 | Bland et al. |
| 2003/0228402 A1 | 12/2003 | Franklin et al. |
| 2004/0026685 A1 | 2/2004 | Ito et al. |
| 2004/0234662 A1 | 11/2004 | Ben-Yehoshua |
| 2004/0266852 A1 | 12/2004 | Coleman |
| 2005/0031744 A1 | 2/2005 | Paliyath et al. |
| 2005/0170052 A1 | 8/2005 | Pimentel |
| 2005/0214291 A1 | 9/2005 | Lee et al. |
| 2006/0034880 A1 | 2/2006 | Christmas et al. |
| 2007/0048344 A1 | 3/2007 | Yahiaoui et al. |
| 2007/0048345 A1 | 3/2007 | Huang et al. |
| 2007/0087094 A1 | 4/2007 | Schuer |
| 2009/0249557 A1 | 10/2009 | Maki et al. |
| 2009/0263549 A1 | 10/2009 | Kleve et al. |
| 2011/0150817 A1 | 6/2011 | Woo et al. |
| 2012/0058075 A1 | 3/2012 | Petrucci et al. |
| 2012/0128843 A1 | 5/2012 | Richardson et al. |
| 2012/0148718 A1 | 6/2012 | Wilson et al. |
| 2012/0164081 A1 | 6/2012 | de Lame et al. |
| 2012/0202867 A1 | 8/2012 | Walter et al. |
| 2012/0252893 A1* | 10/2012 | Pimentel ............... A01N 31/16  514/557 |
| 2014/0323572 A1 | 10/2014 | Pimentel et al. |
| 2015/0208697 A1 | 7/2015 | Richardson et al. |

FOREIGN PATENT DOCUMENTS

| | | | |
|---|---|---|---|
| EP | 0266199 | A2 | 5/1988 |
| EP | 0991327 | A1 | 4/2000 |
| EP | 1214879 | A2 | 6/2002 |
| ES | 2234127 | T3 | 6/2005 |
| ES | 2247701 | T3 | 3/2006 |
| JP | 2000-325037 | A | 11/2000 |
| JP | 2002-511083 | A | 4/2002 |
| JP | 2004-513153 | A | 4/2004 |
| RU | 2332361 | | 8/2008 |
| WO | 95/28091 | A1 | 10/1995 |
| WO | 96/11585 | A1 | 4/1996 |
| WO | 97/28896 | A1 | 8/1997 |
| WO | 99/00025 | A1 | 1/1999 |
| WO | 99/00026 | A1 | 1/1999 |
| WO | 99/60865 | A1 | 12/1999 |
| WO | WO 01/32020 | A2 * | 5/2001 ............ A01N 37/02 |
| WO | WO 01/97799 | | 12/2001 |
| WO | 2002080668 | A2 | 10/2002 |
| WO | 03070181 | A2 | 8/2003 |
| WO | 2008/031087 | A1 | 3/2008 |
| WO | WO 2011/017367 | | 2/2011 |
| WO | 11/025496 | A1 | 3/2011 |

OTHER PUBLICATIONS

Khan et al, "Antagonistic Effect of Fatty Acids Against *Salmonella* in Meat and Bone Meal", Applied Microbiology, Mar. 1969, pp. 402-404, vol. 17 No. 3.

International Search Report for PCT/US2012/059169.

Written Opinion of the International Search Authority for PCT/US2012/059169.

1999, Archbold, D.; Hamilton-Kemp, T.; Clements, A.; Collins, R. Fumigating 'Crimson Seedless' Table Grapes with (E)-2-Hexenal Reduces Mold during Long-term Postharvest Storage. HortScience. 1999, v. 34, No. 4, 705-707).

1994, Andersen, R. A.; Hamilton-Kemp, T.; Hilderbrand, D. F.; McCraken Jr., C. T.; Collins, R. W.; Fleming, P. D. Structure-Antifungal Activity Relationships among Volatile C6 and C9 Aliphatic Aldehydes, Ketones, and Alcohols. J. Agric. Food Chern. 1994, v. 42, 1563-1568.

2007, Belletti, N.; Kamdem, S.; Patrignani, F.; Lanciotti, R.; Covelli, A.; Gardini, F. Antimicrobial Activity of Aroma Compounds against *Saccharomyces cerevisioe* and Improvement of Microbiological Stability of Soft Drinks as Assessed by Logistic Regression. AEM. 2007, v. 73, No. 17, 5580-5586).

2001, Bisignano, G.; Lagana, M. G.; Trombetta, D.; Arena,S.; Nostro, A.; Uccella, N.; Mazzanti, G.; Saija, A. In vitro antibacterial activity of some aliphatic aldehydes from *Olea europaea* L. FEMS Microbiology Letters. 2001, v. 198,9-13.

2004, Ceylan E and D Fung. Antimicrobial Activity of Spices. 1. Ropid Methods in Microbiology. 2004 v.12, 1-55.

2001, Chadeganipour and Haims (2001), Antifungal activities of pelargonic and capric acid on Microsporum gypseum Mycoses v. 44, No. 3-4,109-112.

1993, Deng, W.; Hamilton-Kemp, T.; Nielsen, M.; Anderson, R.; Collins, G.; Hilderbrand, D. Effects of Six-Carbon Aldehydes and Alcohols on Bacterial Proliferation. 1. Agric. Food Chem. 1993, v. 41,506-510.

2005, Dilantha Fernando, W.G., R. Ramaranthnam, A. Krihnamoorthy and S. Savchuck. Identification and use of potential organic antifungal volatiles in biocontrol. 50i/ Biology and Biochemistry. 2005 v.37, 955-964.

1998, Fallik, E. et. al. Trans-2-hexenal can stimulate Botrytis cinerea growth in vitro and on strawberries in vivo during storage, 1. ASHS. 1998, v. 123, No. 5, 875-881.

2001, Gardini, F.; Lanciotti, R; Guerzoni, M.E. Effect of trans-2-hexenal on the growth of Aspergillus flavus in relation to its concentration, temperature and water activity. Letters in App. Microbiology. 2001, v. 33, 50-55.

1971, Gaunt, I. F.; Colley,J. Acute and Short-term Toxicity Studies on trans-2-Hexenal. Fd Cosmet. Toxicol. 1971,v. 9, 775-786.

1191, Hamilton-Kemp, et. al, (1. Agric. Food Chem. 1991, v. 39, No. 5, 952-956.

2001, N. Hirazawa, et. al. (Antiparasitic effect of medium-chain fatty acids against ciliated Crptocaryon irritans infestation in the red sea bream *Pagrus major*, 2001, Aquaculture v. 198, 219-228.

2008, Hubert, J.; Munzbergova, Z.; Santino, A. Plant volatile aldehydes as natural insecticides against stored-product beetles. Pest Monag. Sci. 2008, v. 64, 57-64.

2004, Kim, y. S.; Shin, D. H. Volatile Constituents from the Leaves of Collicarpa japonico Thunb. and Their Antibacterial Activities. 1. Agric. Food Chem. 2004, v. 52,781-787.

1999, Kubo, J; Lee, J. R.; Kubo, I. Anti-Helicobacter pylori Agents from the Cashew Apple. 1. Agric. Food Chem. 1999, v. 47, 533-537.

2001, Kubo, I. and K. Fujita, Naturally Occurring Anti-*Salmonella* Agents. 1. Agric. Food Chem. 2001, v. 49, 5750-5754.

2004, B. Lederer, T. Fujimori., Y. Tsujino, K. Wakabayashi and P Boger, 2004. Phytotoxic activity of middle-chain fatty acids II: peroxidation and membrane effects. Pesticide Biochemistry and Physiology 80: 151-156.

2009, Matasyoh, J.C, Z.C Maiyo, R.R. Ngure and R. Chepkorir. Chemical Composition and Antimicrobial Activity of the Essential Oil of Coriondrum sotivum. Food Chemistry. 2009 v.113, 526-529.

1993, Muroi, H.; Kubo, A.; Kubo, I. Antimicrobial Activity of Cashew Apple Flavor Compounds . . . 1. Agric. Food Chern. 1993, v. 41, 1106-1109.

2002, Nakamura. and Hatanaka Green-leaf-derived C6-aroma compounds with potent antibacterial action that act on both gram-negative and gram-positive bacteria. 1. Agric. Food Chem. 2002, v. 50 No. 26, 7639-7644.

2007, Neri F., Mari, S. Brigati and P. Bertolini, 2007, Fungicidal activity of plant volatile compounds for controlling Monolinia laxa in stone fruit, Plant Disease v. 91,No. 1, 30-35.

2006, Neri, F.; Mari, M.; Menniti, A.; Brigati, S.; Bertolini, P. Control of Penicillium expansum in pears and apples by trans-2-hexenal va pours. Postharvest Bioi. and Tech. 2006, v. 41,101-108.

2006, Neri, F.; Mari, M.; Menniti, A. M.; Brigati, S. Activity of trans-2-hexenal against Penicillium expansum in 'Conference' pears. 1. Appl. Micrbiol. 2006, v. 100, 1186-1193.

2008, Patrignani, F.; lucci, l.; Belletti, N.; Gardini, F.; Guerzoni, M. E.; lanciotti, R. Effects of sub-lethal concentrations of hexanal and 2-(E)-hexenal on membrane fatty acid composition and volatile compounds of Listeria monocytogenes, *Staphylocaccus oureus, Salmonella enteritidis* and *Escherichia cofi*. Internationall. Food Micro. 2008, v.123, 1-8.

1979, Paster, N. 1979, A commercial study of the efficiency of propionic acid and acid and calcium propionate as fungistats in poultry feed, Poult. Sci. v. 58, 572-576.

(56) References Cited

OTHER PUBLICATIONS

2007, Saniewska, S. and M. Saniewski, 2007. The effect of trans-2-hexenal and trans-2-nonenal on the mycelium growth of Phoma narcissi in vitro, ROC1. AR. POln. CCCLXXXIII, Ogrodn. V. 41,189-193.
Mar. 24, 2008, Stout, M. D.; Bodes, E.; Schoon hoven, R.; Upton, P. B.; Travlos, G. S.; Swenberg, J. A. Toxicity, DNA Binding, and Cell Proliferation in Male F344 Rats following Short-term Gavage Exposures to Trans-2-Hexenal. Soc. Toxicologic. Pathology Mar. 24, 2008, 1533-1601 online.
2006, Van Immerseel, F., IB. Russell, M.D. Flythe, I. Gantois, L Timbermont, F. Pasmans, F. Haesebrouck, and R. Ducatelle. 2006. The use of organic acids to combat *Salmonella* in poultry: a mechanistic explanation of the efficacy, Avian Pathology. V. 35, No. 3, 182-188.
Cave, "Effect of Dietary Short- and Medium-Chain Fatty Acids on Feed Intake by Chicks", Poultry Science, 1982, pp. 1147-1153, vol. 61.
Wales et al., "Chemical Treatment of Animal Feed and Water for the Control of *Salmonella*", Foodborne Pathogens and Disease, 2010, pp. 3-15, vol. 7, No. 1.
Brenes et al., "Essential Oils in Poultry Nutrition: Main Effects and Modes of Action", Animal Feed Science and Technology, 2010, pp. 1-14, vol. 158.
"Scientific Opinion on the Safety and Efficacy of Formaldehyde for all Animal Species Based on a Dossier Submitted by Regal BV", EFSA Journal, 2014, vol. 12 Issue 2 No. 3561, 24 pages.
Akbari et al., "Effect of Acetic Acid Administration in Drinking Water on Performance Growth Characteristics and Ileal Microflora of Broiler Chickens", Journal of Science and Technology of Agriculture and Natural Resources, 2004, pp. 148, vol. 3.
Aneja et al., "Trichoderma Harzianum Pproduces Nonanoic Acid, an Inhibitor of Sport Germination and Mycelial Growth of Two Cacao Pathogens", Physiological and Molecular Plant Pathology, 2005, pp. 304-307, vol. 67.
Bard et al., "Geraniol Interferes with Membrane Functions in Strains of Candida and *Saccharomyces*", Lipids, 1988, pp. 534-538, vol. 23 No. 6.
Chaumont et al., "Campaign Against Allergic Moulds in Dwellings, Inhibitor Properties of Essential Oil Geranium Bourbon, Citronello, Geraniol and Citral", Annales Pharmaceutiques Francaises, 1992, pp. 156-166, vol. 50, No. 3.
Elegbede et al., "Inhibition of DMBA-Induced Mammary Cancer by Monoterpene D-Limonene", Carcinogenesis, 1984, pp. 661-664, vol. 5 No. 5.
Elgebede et al., "Regression of Rat Primary Mammary Tumors Following Dietary D-Limonene", Journal of National Cancer Institute, 1986, pp. 323-325, vol. 76 No. 2.
Elson et al., "The Chemoprevention of Cancer by Mevalonate-Derived Constituents of Fruits and Vegetables", Journal of Nutrition, 1994, pp. 607-614, vol. 124.
English Translation of DD Publication 161131 dated Jun. 23, 1981.
English Translation of JP Publication 2000-325037 dated Nov. 28, 2000.
Extended European Search Report for EP 11820383.5 dated Mar. 19, 2014.
Fruijtier-Polloth, "Safety assessment on Polyethylene Glycols (PEGs) and their Derivatives as used in Cosmetic Products", Toxicology, 2005, pp. 1-38, vol. 214.
Gardner et al., "Hexenal, Trans-2-Hexenal, and Trans-2-Nonenal Inhibit Soybean, Glycine Max, Seed Germination", Journal of Agricultural and Food Chemistry, 1990, pp. 1316-1320, vol. 38.
Higgins et al., "Efficacy of Several Organic Acids Against Mold", Journal of Applied Poultry Research, 1999, pp. 480-487, vol. 8.
Hooser et al., "Effects of an Insecticidal Dip Containing D-Limonene in the Cat", Journal of the American Veterinary Medical Association, 1986, pp. 905-908, vol. 189 No. 8, Abstract.
Humphrey et al., "The Vertical Transmission of *Salmonellas* and Formic Acid Treatment of Chicken Feed: A Possible Strategy for Control", Epidemiology and Infection, 1988, pp. 43-49, vol. 100.
International Search Report and Written Opinion for PCT/US2011/047693 dated Mar. 21, 2012.
Ishii, "Antibacterial Activity of Terprenone, a Non Water-Soluble Antiulcer Agent, Against Helicobacter Pylori", International Journal of Medical Microbiology, Virology, Parasitology, and Infectious Diseases, 1993, pp. 239-243, vol. 280, No. 1-2.
Kadota et al., "Antibacterial Activity of Trichorabdal A from Rabdosia Trichocarpa Against Helicobacter Pylori", Zentralblat fur Bakteriologie, 1997, pp. 63-67, vol. 287 No. 1.
Karlson et al., "Inhibition of Tumor Cell Growth by Monoterpenes in Vitro: Evidence of a Ras-Independent Mechanism of Action", Anticancer Drugs, 1996, pp. 422-429, vol. 7 No. 4.
Kim et al., "Antibacterial Activity of Some Essential Oil Components Against Five Foodborne Pathogens", Journal of Agricultural and Food Chemistry, 1995, pp. 2839-2845, vol. 43.
Kishimoto et al., "Direct Fungicidal Activities of C6-Aldehydes are Important Constituents for Defense Responses in *Arabidopsis* Against Botrytis Cinerea", Phytochemistry, 2008, pp. 2127-2132, vol. 69.
Leite, "Evaluation of the Antimicrobial Activity of Citral", Letters in Applied Microbiology, 1989, pp. 105-108, vol. 9 No. 3.
Mikhlin et al., "Antifungal and Antimicrobial Activity of Some Derivatives of Beta-Ionone and Vitamin A", Prikl Biokhim Mikrobiol, 1983, pp. 795-803, vol. 19.
Neri et al., "Activity of Trans-2-Hexenal Against Pencillium Expansum in 'Conference' Pears", Journal of Applied Microbiology, 2006, pp. 1186-1193, vol. 100.
Rahnema et al., "Preservation and Use of Chemically Treated High-Moisture Corn by Weanling Pigs", Journal of Production and Agriculture, 1992, pp. 458-461, vol. 5 No. 4.
Salt et al., "Effects of b-Ionone and Abscisic Acid on the Growth of Tobacco and Resistance to Blue Mold, Mimicry of Effects of Stem Infection by Peronospora Tabacina", Physiological and Molecular Plant Pathology, 1986, pp. 287-297, vol. 28.
Yu et al., "The Efficacy of b-Ionone in the Chemoprevention of Rat Mammary Carcinogenesis", Journal of Agricultural and Food Chemistry, 1995, pp. 2144-2147, vol. 43.
Haque et al., "Proponic Acid is an Alternative to Antibiotics in Poultry Diet", Bangladesh Journal of Animal Science, 2009, pp. 115-122, vol. 38 (1&2).
Ponce De Leon et al., "Effect of Acetic and Citric Acids on the Growth and Activity (VB-N) of *Pseudomonas* sp. and *Moraxella* sp." Bulletin of the Faculty of Fisheries Hokkaido University, May 1993, pp. 80-85, vol. 44, No. 2.
Lin et al, "Comparative Analysis of Extreme Acid Survival in *Salmonella typhimurium, Shigella flexneri,* and *Escherichia coli*", Journal of Bacteriology, Jul. 1995, pp. 4097-4104, vol. 177, No. 14.
Karabinos et al., "Bactericidal Activity of Certain Fatty Acids", The Journal of the American Oil Chemists' Society, Jun. 1954, pp. 228-232, vol. 31.
Opdyke et al., "Fragrance Raw Materials Monographs", Food and Cosmetics Toxicology, 1978, pp. 839-841, vol. 16, Suppl. 1.
Results of Experiments on the Antimicrobial Effects of the Compositions Claimed of Various Microorganisms, Sep. 4, 2017, 1 page.
Opposition against EP2768539, Filed on Sep. 4, 2017, 16 pages.
Opposition against EP3023009, Filed on Sep. 4, 2016, 15 pages.
Written Submission by Opponent in Opposition against EP2768539 filed Oct. 2, 2018, 7 pages.
Written Submission by Opponent in Opposition against EP2768539 filed Oct. 5, 2018, 3 pages.

* cited by examiner

ANTIMICROBIAL FORMULATIONS WITH PELARGONIC ACID

CROSS REFERENCE TO RELATED APPLICATIONS

This application is a national stage entry of PCT/US2012/059169, filed Oct. 8, 2012, which published as WO2013059012 on Apr. 25, 2013, and claims priority to U.S. Provisional application 61/549,661, filed 20 Oct. 2011, entitled "Antimicrobial Formulations with Pelargonic Acid" and is hereby incorporated by reference.

BACKGROUND OF THE INVENTION

1. Field of the Invention

An antimicrobial formulation consisting of a mixture of organic acids and aldehydes where such combination resulted in synergistic response as compared to the addition of high levels of the other component.

2. Background

The Centers for Disease Control and Prevention (CDC) estimates that roughly one out of six Americans or 48 million people are sickened by food borne illnesses each year. Another 128,000 are hospitalized and approximately 3,000 die of food borne disease every year. In a 2011 report the CDC estimated that 20,000 cases of *Salmonella* resulted in hospitalization, and that 378 of these cases resulted in death. It has also estimated that *E. coli* 0157:H7 causes approximately 62,000 cases of food borne disease and approximately 1,800 food borne illness-related hospitalizations in the United States.

A study by the Pew Charitable Trusts of Georgetown University suggested that food borne illnesses cost the United States $152 billion in health-related expenses each year.

As the world trends toward more natural and/or organic antimicrobials, the need to find them has resulted in a great amount of research, as well as increased cost for new raw materials due to the low commercial availability of these new natural/organic products.

Formaldehyde has been use as an antiseptic for many years. Two patents, U.S. Pat. Nos. 5,547,987 and 5,591,467, teach the use of formaldehyde to control *Salmonella* in animal feed. These patents do not suggest that a combination of formaldehyde and an organic acid would provide a synergistic effect, as described in the present invention.

New antimicrobials have been found in many plants. These antimicrobials protect plants from bacterial, fungal, viral and insect infestation. These antimicrobials, which are components of the plant essential oils, can be acidic, alcohol or aldehyde-based chemicals.

One of the volatile compound used in this invention is trans-2-hexenal, which is six-carbon aldehyde with a conjugated double bond, $C_6H_{10}O$ and MW=98.14. Aldehydes are represented by the general formula RCHO, where R is can be hydrogen or an aromatic, aliphatic or a heterocyclic group. They are moderately soluble in water and solubility decreases as the molecular weight increases. Unsaturated aliphatic aldehydes includes, propenal, trans-2-butenal, 2-methyl-2-butenal, 2-methyl-(E)-2-butenal, 2-pentenal, trans-2-hexenal, trans-2-hexen-1-ol, 2-methyl-2-pentanal, 2-isopropylpropenal, 2-ethyl-2-butenal, 2-ethyl-2-hexenal, (Z)-3-hexenal, 3,7-dimethyl-6-octenal, 3,7-dimethyl-2,6-octadienal, (2E)-3,7-dimethyl-2-6-octadienal, (2Z)-3,7-dimethyl-2,6-octadienal, trans-2-nonenal, (2E,6Z)-nonadienal, 10-undecanal, 2-dodecenal, 2,4-hexadienal and others.

Trans-2-hexenal is present in many edible plants such as apples, pears, grapes, strawberries, kiwi, tomatoes, olives, etc. The use of plants and plant extracts have been successful in studies looking for new anti-microbials. For example, cashew apple was effective against *Helicobacter pylori* and *S. cholerasuis* (50-100 ug/ml). The two main components were found to be anacardic acid and trans-2-hexenal. The minimum inhibitory activity and minimum biocidal activity of trans-2-hexenal were determined to be 400 and 800 ug/ml, respectively (Kubo, J.; Lee, J. R.; Kubo, I. Anti-*Helicobacter pylori* Agents from the Cashew Apple. *J. Agric. Food Chem.* 1999, v. 47, 533-537; Kubo, I. And K. Fujita, Naturally Occurring Anti-*Salmonella* Agents. *J. Agric. Food Chem.* 2001, v. 49, 5750-5754). Kim and Shin found that trans-2-hexenal (247 mg/L) was effective against *B. cereus, S. typhimurium, V. parahaemolyticus, L. monocytogenes, S. aureus* and *E. coli* O157:H7 (Kim, Y. S.; Shin, D. H. Volatile Constituents from the Leaves of *Callicarpa japonica* Thunb. and Their Antibacterial Activities. *J. Agric. Food Chem.* 2004, v. 52, 781-787). Nakamura. and Hatanaka (Green-leaf-derived C6-aroma compounds with potent antibacterial action that act on both gram-negative and gram-positive bacteria. *J. Agric. Food Chem.* 2002, v. 50 no, 26, 7639-7644) demonstrated that (3E)-hexenal was effective in controlling *Staphylococcus aureus, E. coli* and *Salmonella typhimurium* at a level of 3-30 ug/ml. Trans-2-hexenal completely inhibited proliferation of both *P. syringae* pathovars (570 ug/L of air) and *E. coli* (930 micrograms/L of air) (Deng, W.; Hamilton-Kemp, T.; Nielsen, M.; Anderson, R.; Collins, G.; Hilderbrand, D. Effects of Six-Carbon Aldehydes and Alcohols on Bacterial Proliferation. *J. Agric. Food Chem.* 1993, v. 41, 506-510). It was observed that trans-2-hexenal at 250 ug/ml was effective at inhibiting the growth of *Phoma* mycelium (Saniewska, S. and M. Saniewski, 2007. The effect of trans-2-hexenal and trans-2-nonenal on the mycelium growth of *Phoma narcissi* in vitro, Rocz. A R. Pozn. CCCLXXXIII, Ogrodn. V. 41, 189-193). In a study to control mold in fruits it was found that trans-2-hexenal was not phytotoxic to apricots, but it was phytotoxic for peaches and nectarines at 40 µL/L (Neri, F., M. Mari, S. Brigati and P. Bertolini, 2007, Fungicidal activity of plant volatile compounds for controlling *Monolinia laxa* in stone fruit, *Plant Disease* v. 91, no. 1, 30-35). Trans-2-hexenal (12.5 µL/L) was effective on controlling *Penicillium expansum* that causes blue mold (Neri, F.; Mari, M.; Menniti, A.; Brigati, S.; Bertolini, P. Control of *Penicillium expansum* in pears and apples by trans-2-hexenal vapours. *Postharvest Biol. and Tech.* 2006, v. 41, 101-108. Neri, F.; Mari, M.; Menniti, A. M.; Brigati, S. Activity of trans-2-hexenal against *Penicillium expansum* in 'Conference' pears. *J. Appl. Micrbiol.* 2006, v. 100, 1186-1193). Fallik, E. et. al. (Trans-2-hexenal can stimulate *Botrytis cinerea* growth in vitro and on strawberries in vivo during storage, *J. ASHS.* 1998, v. 123, no. (5, 875-881) and Hamilton-Kemp, et. al, (*J. Agric. Food Chem.* 1991, v. 39, no. 5, 952-956) suggested that trans-2-hexenal vapors inhibited the germination of *Botrytis* spores and apple pollen.

US Published Application No. 2007/0087094 suggests the use of at least two microbiocidally active GRAS compounds in combination with less than 50% alcohol (isopropanol or isopropanol/ethanol) as a microbicide. Trans-2-hexenal could be considered one of the GRAS compounds (Schuer. Process for Improving the Durability of, and/or Stabilizing, Microbially Perishable Products. US Published Application No. 2007/0087094). Also, Archbold et. al. observed that the use of 2-hexenal at 0.86 or 1.71 mmol (100 or 200 microliters neat compound per 1.1 L container, respectively) for 2 weeks as for postharvest fumigation of seedless table grapes showed promise for control of mold (Archbold, D.; Hamilton-Kemp, T.; Clements, A.; Collins, R. Fumigating 'Crimson Seedless' Table Grapes with (E)-2-Hexenal Reduces Mold during Long-term Postharvest Storage. *HortScience.* 1999, v. 34, no. (4, 705-707).

U.S. Pat. No. 5,698,599 suggests a method to inhibit mycotoxin production in a foodstuff by treating it with trans-2-hexenal. Trans-2-hexenal completely inhibited the growth of *A. flavus, P. notatum, A. alternate, F. oxysporum, Cladosporium* species, *B. subtilis* and *A. tumerfaciens* at a concentration of 8 ng/L air. When comparing trans-2-hexenal to citral in controlling yeast ($10^5$ CFU/bottle) in beverages it was found that 25 ppm of trans-2-hexenal and thermal treatment (56° C. for 20 min) was equivalent to 100-120 ppm citral. In beverages that were not thermally treated, 35 ppm of trans-2-hexenal was necessary to stabilize them (Belletti, N.; Kamdem, S.; Patrignani, F.; Lanciotti, R.; Covelli, A.; Gardini, F. Antimicrobial Activity of Aroma Compounds against *Saccharomyces cerevisiae* and Improvement of Microbiological Stability of Soft Drinks as Assessed by Logistic Regression. *AEM.* 2007, v. 73, no. 17, 5580-5586). Not only has trans-2-hexenal has been used as antimicrobial but also been observed to be effective in the control of insects. Volatiles (i.e. trans-2-hexenal) were effective against beetles such as *Tibolium castaneum, Rhyzopertha dominica, Sitophilus granaries, Sitophilus orazyzae* and *Cryptolestes perrugineus* (Hubert, J.; Munzbergova, Z.; Santino, A. Plant volatile aldehydes as natural insecticides against stored-product beetles. *Pest Manag. Sci.* 2008, v. 64, 57-64). U.S. Pat. No. 6,201,026 (Hammond et al. Volatile Aldehydes as Pest Control Agents) suggests of an organic aldehyde of 3 or more carbons for the control of aphides.

Several patents suggest the use of trans-2-hexenal as a fragrance or perfume. U.S. Pat. No. 6,596,681 suggests the use of trans-2-hexenal as a fragrance in a wipe for surface cleaning. U.S. Pat. Nos. 6,387,866, 6,960,350 and 7,638,114 suggest the use of essential oil or terpenes (for example trans-2-hexenal) as perfume for antimicrobial products. U.S. Pat. No. 6,479,044 demonstrates an antibacterial solution comprising an anionic surfactant, a polycationic antibacterial and water, where an essential oil is added as perfume. This perfume could be a terpene such as trans-2-hexenal or other type of terpenes. U.S. Pat. Nos. 6,323,171, 6,121,224 and 5,911,915 demonstrate an antimicrobial purpose microemulsion containing a cationic surfactant where an essential oil is added as a perfume. This perfume can contain various terpenes including trans-2-hexenal. U.S. Pat. No. 6,960,350 demonstrates an antifungal fragrance where a synergistic effect was found when different terpenes were used in combinations (for example trans-2-hexenal with benzaldehyde).

The mode of action of trans-2-hexenal is thought to be alteration of the cell membrane due to a reaction of the unsaturated aldehyde with sulfhydryl or cysteine residues, or the formation of Schiff bases with amino groups in peptides and proteins (Deng, W.; Hamilton-Kemp, T.; Nielsen, M.; Anderson, R.; Collins, G.; Hilderbrand, D. Effects of Six-Carbon Aldehydes and Alcohols on Bacterial Proliferation. *J. Agric. Food Chem.* 1993, v. 41, 506-510). Trans-2-hexenal is reported to act as a surfactant but it likely permeates by passive diffusion across the plasma membrane. Once inside the cells, its $\alpha,\beta$-unsaturated aldehyde moiety reacts with biologically important nucleophilic groups. This aldehyde moiety is known to react with sulphydryl groups mainly by 1,4-addition under physiological conditions (Patrignani, F.; Lucci, L.; Belletti, N.; Gardini, F.; Guerzoni, M. E.; Lanciotti, R. Effects of sub-lethal concentrations of hexanal and 2-(E)-hexenal on membrane fatty acid composition and volatile compounds of *Listeria monocytogenes, Staphylococcus aureus, Salmonella enteritidis* and *Escherichia coli. International J. Food Micro.* 2008, v. 123, 1-8).

It was suggested that the inhibition of *Salmonella typhimurim* and *Staphylococcus aureus* by trans-2 hexenal is due to the hydrophobic and hydrogen bonding of its partition in the lipid bilayer. The destruction of electron transport systems and the perturbation of membrane permeability have also been suggested as modes of action (Gardini, F.; Lanciotti, R.; Guerzoni, M. E. Effect of trans-2-hexenal on the growth of *Aspergillus flavus* in relation to its concentration, temperature and water activity. *Letters in App. Microbiology.* 2001, v. 33, 50-55). The inhibition of *P. expansum* decay may be due to damage to fungal membranes of germinating conidia. (Neri, F.; Mari, M.; Menniti, A.; Brigati, S.; Bertolini, P. Control of *Penicillium expansum* in pears and apples by trans-2-hexenal vapours. *Postharvest Biol. and Tech.* 2006, v. 41, 101-108; Neri, F.; Mari, M.; Menniti, A. M.; Brigati, S. Activity of trans-2-hexenal against *Penicillium expansum* in 'Conference' pears. *J. Appl. Micrbiol.* 2006, v. 100, 1186-1193).

Studies have been performed to compare trans-2-hexenal to similar compounds. Deng et. al. showed that unsaturated volatiles, trans-2-hexenal and trans-2-hexen-1-ol, exhibited a greater inhibitory effect than the saturated volatiles, hexanal and 1-hexanol (Deng, W.; Hamilton-Kemp, T.; Nielsen, M.; Anderson, R.; Collins, G.; Hilderbrand, D. Effects of Six-Carbon Aldehydes and Alcohols on Bacterial Proliferation. *J. Agric. Food Chem.* 1993, v. 41, 506-510). Trans-2-hexenal was more active than hexanal, nonanal and trans-2-octenal against all ATCC bacterial strains (Bisignano, G.; Lagana, M. G.; Trombetta, D.; Arena, S.; Nostro, A.; Uccella, N.; Mazzanti, G.; Saija, A. In vitro antibacterial activity of some aliphatic aldehydes from *Oleo europaea* L. *FEMS Microbiology Letters.* 2001, v. 198, 9-13). Others have found that (E)-2-hexenal had lower minimal fungal-growth-inhibiting concentrations than hexanal, 1-hexanol, (E)-2-hexen-1-ol, and (Z)-3-hexen-1-ol as determined for several species of molds, basically aldehydes>ketones>alcohols (Andersen, R. A.; Hamilton-Kemp, T.; Hilderbrand, D. F.; McCraken Jr., C. T.; Collins, R. W.; Fleming, P. D. Structure—Antifungal Activity Relationships among Volatile $C_6$ and $C_9$ Aliphatic Aldehydes, Ketones, and Alcohols. *J. Agric. Food Chem.* 1994, v. 42, 1563-1568). Hexenal and hexanoic acid were more effective than hexanol in inhibiting *salmonella* (Kubo, I. And K. Fujita, Naturally Occurring Anti-*Salmonella* Agents. *J. Agric. Food Chem.* 2001, v. 49, 5750-5754).

Muroi et al suggested that trans-2-hexenal exhibited broad antimicrobial activity but its biological activity (50 to 400 µg/mL) is usually not potent enough to be considered for practical applications (Muroi, H.; Kubo, A.; Kubo, I. Antimicrobial Activity of Cashew Apple Flavor Compounds. *J. Agric. Food Chem.* 1993, v. 41, 1106-1109). Studies have shown that trans-2-hexenal can potentiate the effectiveness of certain types of antimicrobials. Several patents suggest the use of potentiators for aminoglycoside antibiotics (U.S. Pat. No. 5,663,152), and potentiators for polymyxin antibiotic (U.S. Pat. Nos. 5,776,919 and 5,587,358). These potentiators can include indol, anethole, 3-methylindole, 2-hydroxy-6-R-benzoic acid or 2-hexenal. A strong synergic effect was observed when trans-2-eptenal, trans-2-nonenal, trans-2-decenal and (E,E)-2,4-decadienal were tested together (1:1:1:1 ratio) against ATCC and clinically isolated microbial strains (Bisignano, G.; Lagana, M. G.; Trombetta, D.; Arena, S.; Nostro, A.; Uccella, N.; Mazzanti, G.; Saija, A. In vitro antibacterial activity of some aliphatic aldehydes from *Oleo europaea* L. *FEMS Microbiology Letters.* 2001, v. 198, 9-13).

Humans are exposed daily to trans-2-hexenal through consumption of food and beverages. Human exposures to trans-2-hexenal are ~350 µg/kg/day, with 98% derived from natural sources and 2% from artificial flavoring. It is unlikely that trans-2-hexenal would be toxic to humans since toxic levels in rats are 30 times higher than normal intake by humans (Stout, M. D.; Bodes, E.; Schoonhoven, R.; Upton, P. B.; Travlos, G. S.; Swenberg, J. A. Toxicity, DNA Binding, and Cell Proliferation in Male F344 Rats following Short-term Gavage Exposures to Trans-2-Hexenal. *Soc. Toxicologic. Pathology* Mar. 24 2008, 1533-1601 online). In another rat study, feeding trans-2-hexenal at dietary levels of 0 (control), 260, 640, 1600 or 4000 ppm fed for 13 wk did not induce any changes in hematological parameters or organ weights. At 4000 ppm there was a reduction in body weight and intake, but it was not significant (Gaunt, I. F.; Colley, J. Acute and Short-term Toxicity Studies on trans-2-Hexenal. *Fd Cosmet. Toxicol.* 1971, v. 9, 775-786).

Even in fruits, twenty four hours to seven days exposure of pears and apples to trans-2-hexenal (12.5 µL/L did not affect fruit appearance, color, firmness, soluble solids content or titratable acidity. In a trained taste panel, no significant differences in the organoleptic quality of untreated and trans-2-hexenal treated "Golden Delicious" apples were observed, while maintenance of off-flavors was perceived in "Bartlett", "Abate Fetel" and "Royal Gala" fruit (Neri, F.; Mari, M.; Menniti, A.; Brigati, S.; Bertolini, P. Control of *Penicillium expansum* in pears and apples by trans-2-hexenal vapours. *Postharvest Biol. and Tech.* 2006, 41, 101-108; Neri, F.; Mari, M.; Menniti, A. M.; Brigati, S. Activity of trans-2-hexenal against *Penicillium expansum* in 'Conference' pears. *J. Appl. Micrbiol.* 2006, v. 100, 1186-1193).

Citral and cinnamaldehyde, have been found to be antifungal. The mode of action of these aldehydes is by reacting with the sulfur group (—SH) from fungi (Ceylan E and D Fung. Antimicrobial Activity of Spices. *J. Rapid Methods in Microbiology.* 2004 v. 12, 1-55).

U.S. Pat. No. 6,750,256 and RE 39543 suggest the use of aromatic aldehydes like α-hexyl cinnamic aldehyde for the control of ant population but does not suggest any synergistic effect of the aldehyde in combination with a organic acid to improve effectiveness or a reduction on the active ingredient or their effectiveness on bacterial control.

The essential oil of *Coriandrum sativum* contains 55.5% of aldehydes which has been effective on preventing growth of gram positive and gram negative bacteria. These aldehydes include: n-octanal, nonanal, 2E-hexenal, decanal, 2E-decenal, undecenal, dodecanal, 2E-dodecenal, tridecanal, 2E-tridecene-1-al and 3-dodecen-1-al (Matasyoh, J. C., Z. C. Maiyo, R. R. Ngure and R. Chepkorir. Chemical Composition and Antimicrobial Activity of the Essential Oil of *Coriandrum sativum. Food Chemistry.* 2009 v. 113, 526-529).

Furfural, a cyclic aldehyde, is currently used as fungicide and nematicide but there are no reports of its use in combination with an organic acid i.e., nonanoic acid, as demonstrated in the present invention.

Two aldehydes, n-decanal and nonanal were effective at controlling fungal growth (Dilantha Fernando, W. G., R. Ramaranthnam, A. Krihnamoorthy and S. Savchuck. Identification and use of potential organic antifungal volatiles in biocontrol. *Soil Biology and Biochemistry.* 2005 v. 37, 955-964)

The prior art has not suggested or observed that the use of aldehydes in combination with organic acids improved the antimicrobial activity of either of the components by themselves. It has suggested synergy with the combination of essential oils and as potentiators of antibiotics.

Commercial mold inhibitors and bactericides are composed of single organic or a mixture of organic acids and formaldehyde. These acids are primarily propionic, benzoic acid, butyric acid, acetic, and formic acid. Organic acids have been a major additive to reduce the incidence of food borne infections. The mechanism by which small chain fatty acids exert their antimicrobial activity is that undissociated (RCOOH=non-ionized) acids are lipid permeable and in this way they can cross the microbial cell wall and dissociate in the more alkaline interior of the microorganism (RCOOH-> $RCOO^-+H^+$) making the cytoplasm unstable for survival. (Van Immerseel, F., J. B. Russell, M. D. Flythe, I. Gantois, L. Timbermont, F. Pasmans, F. Haesebrouck, and R. Ducatelle. 2006. The use of organic acids to combat *Salmonella* in poultry: a mechanistic explanation of the efficacy, *Avian Pathology.* v. 35, no. 3, 182-188; Paster, N. 1979, A commercial study of the efficiency of propionic acid and acid and calcium propionate as fungistats in poultry feed, Poult. Sci. v. 58, 572-576).

Pelargonic acid (nonanoic acid) is a naturally occurring fatty acid. It is an oily, colorless fluid, which at lower temperature becomes solid. It has a faint odor compared to butyric acid and is almost insoluble in water. Pelargonic acid has been used as a non-selective herbicide. Scythe (57% pelargonic acid, 3% related fatty acids and 40% inert material) is a broad-spectrum post-emergence or burn-down herbicide produced by Mycogen/Dow Chemicals. The herbicidal mode of action of pelargonic acid is due first to membrane leakage during darkness and daylight and second to peroxidation driven by radicals originating during daylight by sensitized chlorophyll displaced from the thylakoid membrane (B. Lederer, T. Fujimori., Y. Tsujino, K. Wakabayashi and P Boger, 2004. Phytotoxic activity of middle-chain fatty acids II: peroxidation and membrane effects. *Pesticide Biochemistry and Physiology* 80: 151-156).

Chadeganipour and Haims (2001) showed that the minimum inhibitory concentration (MIC) of medium chain fatty acids to prevent growth of *M. gypseum* was 0.02 mg/ml capric acid and for pelargonic acid 0.04 mg/ml on solid media and 0.075 mg/ml capric acid and 0.05 mg/ml pelargonic in liquid media. These acids were tested independently and not as a mixture (Antifungal activities of pelargonic and capric acid on *Microsporum gypseum*" Mycoses v. 44, no 3-4, 109-112). N. Hirazawa, et. al. (Antiparasitic effect of medium-chain fatty acids against ciliated *Crptocaryon irritans* infestation in the red sea bream *Pagrus major,* 2001, *Aquaculture* v. 198, 219-228) found that nonanoic acid as well as C6 to C10 fatty acids were effective in controlling the growth of the parasite *C. irritans* and that C8, C9 and C19 were the more potent. It was found that *Trichoderma harzianum*, a biocontrol for cacao plants, produces pelargonic acid as one of many chemicals, which was effective in controlling the germination and growth of cacao pathogens. (M Aneja, T. Gianfagna and P. Hebbar, 2005).

Several US patents disclose the use of pelargonic acids as fungicides and bactericides: US Published Application 2004/026685 discloses a fungicide for agricultural uses that is composed of one or more fatty acids and one or more organic acids different from the fatty acid. In the mixture of the organic acids and the fatty acids, the organic acid acts as a potent synergist for the fatty acid to function as a fungicide. U.S. Pat. No. 5,366,995 discloses a method to eradicate fungal and bacterial infections in plants and to enhance the activity of fungicides and bactericides in plants through the use of fatty acids and their derivatives. This formulation contains 80% pelargonic acid or its salts for the control of plants fungi. The fatty acids used are primarily C9 to C18. U.S. Pat. No. 5,342,630 discloses a novel pesticide for plant use containing an inorganic salt that enhance the efficacy of C 8 to C22 fatty acids. One of the examples shows a powdered product with 2% pelargonic acid, 2% capric acid, 80% talc, 10% sodium carbonate and 5% potassium carbonate. U.S. Pat. No. 5,093,124 discloses a fungicide and arthropodice for plants comprising of alpha mono carboxylic acids and their salts. Preferably the fungicide consists of the C9 to C10 fatty acids, partially neutralized by active alkali metal such as potassium. The mixture described consists of 40% active ingredient dissolved in water and includes 10% pelargonic, 10% capric acid and 20% coconut fatty acids, all of with are neutralized with potassium hydroxide. U.S. Pat. No. 6,596,763 discloses a method to control skin infection comprised of C6 to C18 fatty acids or their derivatives. U.S. Pat. Nos. 6,103,768 and 6,136,856 discloses the unique utility of fatty acids and derivatives to eradicate existing fungal and bacterial infections in plants. This method is not preventive but showed effectiveness in already established infections. Sharpshooter, a commercially available product, with 80% pelargonic acid, 2% emulsifier and 18% surfactant showed effectiveness against *Penicillium* and *Botrytis* spp. U.S. Pat. No. 6,638,978 discloses an antimicrobial preservative composed of a glycerol fatty acid ester, a binary mixture of fatty acids (C6 to C18) and a second fatty acid (C6 to C18) where the second fatty acid is different from the first fatty acid for preservation of food. WO 01/97799 discloses the use of medium chain fatty acids as antimicrobials agents. It shows that an increase of the pH from 6.5 to 7.5 increased the MIC of the short chain fatty acids containing 6-8 carbons chain.

Pelargonic acid is used as a component of a food contact surface sanitizing solution in food handling establishments. A product from EcoLab consist of 6.49% pelargonic acid as active ingredient to be use as a sanitizer for all food contact surfaces (12CFR178.1010 b). The FDA has cleared pelargonic acid as a synthetic food flavoring agent (21 CFR 172.515), as an adjuvant, production aid and sanitizer to be used in contact food (12 CFR 178.1010 b) and in washing or to assist in lye peeling of fruits and vegetables (12 CFR 173.315). Pelargonic acid is listed by the USDA under the USDA list of Authorized Substances, 1990, section 5.14, Fruit and Vegetable Washing Compounds.

The present invention relates only to the use of some of the aldehydes extracted from plants or chemically synthesized that synergistically improve the antimicrobial capacity of these compounds by the addition of organic acids especially nonanoic acid.

SUMMARY OF THE INVENTION

One object of the present invention is to provide a composition that synergistically improves the microbicidal effect of organic acids and aldehydes.

The composition can be a solution comprising of an organic acid or a mixture of several organic acids in combination of aldehydes.

The composition can further comprise a volatile aldehyde resulting from the lipoxygenase pathway.

The aldehydes of the composition comprise butyraldehyde, undecylenic aldehyde, citral, decanal, decenal, 2-4-decadienal and other aldehydes from C1 to C24 carbon length or shape.

The organic acids of the composition comprise organic acids of 1 to 24 carbon chain length, saturated, unsaturated, cyclic or other organic acid.

The effective mixture of the invention comprising 1 to 70% by volume organic acids, The effective mixture of the invention comprising 0 to 70% by volume pelargonic acid.

The effective mixture of the invention comprising 5 to 50% aldehyde.

The effective mixture of the invention comprising 0 to 70% by volume water.

The composition is effective against various fungi present in feed and major feed ingredients.

The composition is effective against various bacteria present in feed and major feed ingredients.

The composition is effective against various bacteria and fungi present in water.

The composition is effective against microbes detrimental for the production of alcohol from fermentation of cellulose, starch or sugars.

DESCRIPTION OF THE PREFERRED EMBODIMENTS

In this specification and in the claims which follow, reference will be made to a number of terms which shall be defined to have the following meanings.

Definitions

A "volume percent" of a component is based on the total volume of the formulation or composition in which the component is included.

An organic acid of the composition can comprise formic, acetic, propionic, butyric, pelargonic, lactic and other $C_2$ to $C_{24}$ fatty acid or mono-, di-, or triglycerides containing $C_1$ to $C_{24}$ fatty acids. These fatty acids comprising small chain, medium chain, long chain fatty acids or small chain, medium chain, long chain triglycerides.

The term "effective amount" of a compound means an amount capable of performing the function of the compound or property for which an effective amount is expressed, such as a non-toxic but sufficient amount of the compound to provide the desired antimicrobial benefits. Thus an appropriate effective amount may be determined by one of ordinary skill in the art using only routine experimentation.

Formulations can vary not only in the concentration of major components i.e. organic acids, but also in the type of aldehydes and water concentration used. This invention can be modified in several ways by adding or deleting from the formulation the type of organic acid and aldehyde.

By the terms "synergistic effect or synergy" of the composition is meant to the improved the preservative effect when the ingredients are added as a mixture rather than as individual components.

Composition (s)

A composition of the present invention comprises an effective amount of organic acids of 1 to 24 carbons chain and an aldehyde.

The composition can comprise 1 to 100% by volume organic acids, 0 to 99% by volume acetic acid, 0 to 99% by volume propionic acid, 0 to 99% lactic acid, 0 to 99% pelargonic acid. The composition can comprise 0 to 99% water. The composition can comprise 0 to 99% of other aldehyde.

Methods

The present invention is effective against bacteria and fungi.

The present invention is applied to water.

The present invention is applied to the raw material before entering the mixer.

The present invention is applied to the unmixed raw materials in the mixer.

The present invention is applied during the mixing of the raw ingredients.

The present invention is applied in liquid form or as a dry product mixed with a carrier.

The present invention is applied is such a form that provides a uniform and homogeneous distribution of the mixture throughout the feed.

One of the objectives of the present invention is to control the level of microbes in feed and feedstuffs. Several mixtures of organic acids and aldehydes resulted in several formulations that showed effectiveness against bacteria in buffer and feed. Other objective of the present invention is to formulate an antimicrobial with natural occurring compounds or safe to use compounds. All of the chemicals used in the present invention are currently approved for human uses as antimicrobials, flavor enhancers and perfumery.

There were unexpected results, i.e. synergism and additive effect, when the organic acids and aldehydes were used.

Throughout this application, various publications are referenced. The disclosures of these publications in their entireties are hereby incorporated by reference into this application in order to more fully describe the state of the art to which this invention pertains.

Example 1

Formaldehyde and/or pelargonic acid were added to test tubes at concentrations shown in Table 1. Solutions were vortexed for 10 seconds to ensure mixing. There were three replicate tubes per treatment. A suspension of *Salmonella typhimurium* ($10^3$ cfu/ml, ATCC #14028) was added to three test tubes containing each formulation. The solutions were vortexed, incubated at room temperature for 24 hours plated on SMA (Standard Methods Agar) for 24 hours before counting *Salmonella* colonies. The effectiveness of each formulation as a percent reduction compared to its control value is shown in the following table.

TABLE 1

Interaction of Pelargonic acid and formaldehyde

| Test Product | Formaldehyde (%) | Pelargonic acid (%) | *Salmonella* % reduction |
| --- | --- | --- | --- |
| Control | 0 | 0 | 0 |
| Formaldehyde | 0.025 | 0 | 90.8 |
|  | 0.0125 | 0 | 59.0 |
|  | 0.00625 | 0 | 39.3 |
|  | 0.00312 | 0 | 17.3 |
| Pelargonic acid | 0 | 0.0025 | 0 |
|  | 0 | 0.00125 | 0 |
|  | 0 | 0.000625 | 0 |
|  | 0 | 0.000312 | 0 |
| HCHO: Pelargonic | 0.025 | 0.0025 | 94.2 |
|  | 0.0125 | 0.0025 | 61.0 |
|  | 0.00625 | 0.0025 | 40.7 |
|  | 0.00312 | 0.0025 | 26.1 |
|  | 0.025 | 0.00125 | 92.5 |

TABLE 1-continued

Interaction of Pelargonic acid and formaldehyde

| Test Product | Formaldehyde (%) | Pelargonic acid (%) | *Salmonella* % reduction |
| --- | --- | --- | --- |
|  | 0.0125 | 0.00125 | 52.5 |
|  | 0.00625 | 0.00125 | 38.6 |
|  | 0.00312 | 0.00125 | 27.8 |
|  | 0.025 | 0.000625 | 83.1 |
|  | 0.0125 | 0.000625 | 54.6 |
|  | 0.00625 | 0.000625 | 45.4 |
|  | 0.00312 | 0.000625 | 18.6 |
|  | 0.025 | 0.000312 | 90.2 |
|  | 0.0125 | 0.000312 | 57.6 |
|  | 0.00625 | 0.000312 | 39.7 |
|  | 0.00312 | 0.000312 | 22.7 |

A dose response curve was observed with formaldehyde and the formaldehyde: pelargonic acid treatments. Pelargonic acid at the highest dose tested was not bactericidal. Pelargonic acid at 0.00125 and 0.0025% did appear to increase the effectiveness of formaldehyde.

Example 2

Formaldehyde and/or pelargonic acid were added to test tubes at concentrations shown in Table 2. Solutions were vortexed for 10 seconds to ensure mixing. There were three replicate tubes per treatment. A suspension of *Salmonella typhimurium* ($10^3$ cfu/ml, ATCC #14028) was added to three test tubes containing each formulation. The solutions were vortexed, incubated at room temperature for 24 hours and plated on SMA (Standard Methods Agar) for 24 hours before counting *Salmonella* colonies. The effectiveness of each formulation as a percent reduction compared to its control value is shown in the following table.

TABLE 2

Interaction of pelargonic acid and formaldehyde

| Test Product | Formaldehyde (%) | Pelargonic acid (%) | *Salmonella* % reduction |
| --- | --- | --- | --- |
| Control | 0 | 0 | 0 |
| Formaldehyde | 0.025 | 0 | 88.3 |
|  | 0.0125 | 0 | 50.5 |
|  | 0.00625 | 0 | 41.0 |
|  | 0.00312 | 0 | 17.7 |
| Pelargonic acid | 0 | 0.01 | 100 |
|  | 0 | 0.005 | 96.5 |
|  | 0 | 0.0025 | 8.8 |
|  | 0 | 0.00125 | 2.1 |
| HCHO: Pelargonic | 0.025 | 0.01 | 100 |
|  | 0.025 | 0.005 | 98.6 |
|  | 0.025 | 0.0025 | 97.2 |
|  | 0.025 | 0.00125 | 91.9 |
|  | 0.0125 | 0.01 | 100 |
|  | 0.0125 | 0.005 | 100 |
|  | 0.0125 | 0.0025 | 62.9 |
|  | 0.0125 | 0.00125 | 37.8 |
|  | 0.00625 | 0.01 | 100 |
|  | 0.00625 | 0.005 | 99.6 |
|  | 0.00625 | 0.0025 | 20.8 |
|  | 0.00625 | 0.00125 | 38.2 |
|  | 0.00312 | 0.01 | 100 |
|  | 0.00312 | 0.005 | 97.2 |
|  | 0.00312 | 0.0025 | 36.0 |
|  | 0.00312 | 0.00125 | 0.4 |

A dose response curve was observed with formaldehyde, pelargonic acid and the formaldehyde:pelargonic acid treatments. Pelargonic acid at 0.00125% and 0.0025% did not have a significant impact on *Salmonella* reduction. However, when these levels of pelargonic acid were mixed with formaldehyde, the bactericidal efficacy of formaldehyde was improved.

Example 3

Five formulations were prepared for in vitro studies as presented in Table 3. Formulations were added to test tubes at concentrations of 0.01% and 0.05%. Solutions were vortexed for 10 seconds to ensure mixing. There were three replicate tubes per treatment.

TABLE 3

Chemical Composition of Product Formulas (%)

| Chemical | 1 | 2 | 3 | 4 | 5 |
|---|---|---|---|---|---|
| Acetic acid | 20 | 20 | 20 | 20 | 20 |
| Propionic acid | 50 | 50 | 50 | 50 | 50 |
| Pelargonic acid | 5 | 10 | 15 | 20 | 25 |
| Trans-2-Hexenal | 25 | 20 | 15 | 10 | 5 |
| TOTAL | 100.0 | 100.0 | 100.0 | 100.0 | 100.0 |

A suspension of *Salmonella typhimurium* ($10^4$ cfu/ml) was added to three test tubes containing the different dilutions of each formulation. The tubes were vortexed, incubated at room temperature for 24 hours and then the solution was plated on SMA (Standard Methods Agar) for 48 hours before counting *Salmonella* colonies. The effectiveness of each formulation is reported as a percent reduction compared to its control value as is shown in the following table.

TABLE 4

Percent *Salmonella* Reduction

| Treatment | 0.01% Dilution | 0.05% Dilution |
|---|---|---|
| Formula 1 | 80.6 | 100 |
| Formula 2 | 73.0 | 99.5 |
| Formula 3 | 52.3 | 97.7 |
| Formula 4 | 41.4 | 96.8 |
| Formula 5 | 18.9 | 93.7 |

Pelargonic acid at 10% increases the efficacy of trans-2-hexenal.

Example 4

Three formulations from study 3 were chosen to test their effectiveness against *Salmonella typhimurium* (ATCC #14028) in feed. Poultry mash feed was amended with a meat and bone meal inoculum of *Salmonella typhimurium* at a level of $10^3$ cfu/g of feed. Contaminated feed was then treated with either 0, 1.5 or 2 kg/MT of the formulations listed below. After 24 hours, 10 g of subsamples of the untreated and treated feed were suspended in 90 ml Butterfield buffer. Dilutions were plated on XLT-4 agar and incubated at 37° C. for 48 hours before counting *Salmonella* colonies. Additional samples were taken at 7 days after treatment for *Salmonella* enumeration. The formulas used are shown in the following table.

TABLE 5

CHEMICAL FORMULATIONS (%)

| Chemical | 1 | 2 | 3 |
|---|---|---|---|
| Acetic acid | 20 | 20 | 20 |
| Propionic acid | 50 | 50 | 50 |
| Pelargonic acid | 5 | 10 | 15 |
| Trans-2-hexenal | 25 | 20 | 15 |
| Total | 100 | 100 | 100 |

Results: The following table shows that all formulations were effective against *Salmonella*. Increasing the level of pelargonic acid resulted in similar efficacy as high level of hexenal.

TABLE 6

Effect of Chemicals on *Salmonella* at 1 and 7 Days Post-Treatment

| Treatment | Kg/MT | % Reduction at 1 Day | % Reduction at 7 Day |
|---|---|---|---|
| Control | 0 | 0 | 0 |
| Formula #1 | 1.5 | 85.0 | 97.4 |
|  | 2 | 93.8 | 98.9 |
| Formula #2 | 1.5 | 75.6 | 94.3 |
|  | 2 | 98.0 | 99.6 |
| Formula #3 | 1.5 | 90.6 | 92.1 |
|  | 2 | 91.8 | 96.6 |

Example 5

The five formulations used in Example 3 were chosen to test their effectiveness against *Salmonella typhimurium*. Poultry mash feed was amended with a meat and bone meal inoculum of *Salmonella typhimurium*. Contaminated feed was then treated with either 0 or 2 kg/MT of the formulations. After 24 hours, 10 g of subsamples of the treated feed were suspended in 90 ml Butterfield buffer. Dilutions were plated on XLT-4 agar and incubated at 37° C. for 48 hours before counting *Salmonella* colonies. Additional samples were taken 7 days after treatment for *Salmonella* enumeration. The following table shows that all formulations were effective against *Salmonella*.

TABLE 7

Effect of Chemicals on *Salmonella* at 1 and 7 Days Post-Treatment

| Treatment | % Reduction at 24 Hours | % Reduction at 7 Days |
|---|---|---|
| Control | 0 | 0 |
| Formula 1 | 90.0 | 96.6 |
| Formula 2 | 92.6 | 97.6 |
| Formula 3 | 86.1 | 91.0 |
| Formula 4 | 47.3 | 76.5 |
| Formula 5 | 55.1 | 66.7 |

Equal concentration of Pelargonic acid and trans-2-hexenal resulted in similar effectiveness as high levels (25%) trans-2-hexenal.

Example 6

Formula 1 from Example 3 composed of 25% trans-2-hexenal, 5% pelargonic acid and 70% aqueous organic acids was compared to trans-2-hexenal for residual activity in feed. Poultry mash feed was treated with 0.1, 0.25, 0.5 or 1.0 kg/ton of hexenal compared to 1 kg/ton of the hexenal: pelargonic acid combination product (0.25 kg/ton of hexenal), At 1, 6 and 13 days post treatment, feed was contaminated with a meat and bone meal inoculum of *Salmonella typhimurium* at a level of $10^3$ cfu/g of feed. After 24 hours, 10 g of subsamples of the untreated and treated feed were suspended in 90 ml Butterfield buffer. Dilutions were plated on XLT-4 agar and incubated at 37° C. for 48 hours before counting *Salmonella* colonies.

The following table compares the impact of pelargonic acid on the residual activity of hexenal against *Salmonella*.

TABLE 8

Evaluating the Synergism of Pelargonic acid and Hexenal on Residual Activity in Treated Feed

| Treatment | % Reduction at 13 Days |
|---|---|
| Control | 0 |
| Hexenal: pelargonic mixture (0.25 kg/ton hexenal) | 93.5 |
| 0.10 kg/ton hexenal | 0 |
| 0.25 kg/ton hexenal | 0 |
| 0.50 kg/ton hexenal | 77.4 |
| 1.00 kg/ton hexenal | 87.1 |

The addition of pelargonic acid (5%) to trans-2-hexenal resulted in better effectiveness against *Salmonella* than trans-2-hexenal by itself.

Example 7

Seven aldehydes (butyraldehyde, citral, undecylenic aldehyde, decadienal, cinnamaldehyde, decanal and furfural) were blended with trans-2-hexenal, pelargonic acid, propionic acid and acetic acid as presented in Table 9. A 20% (X-1) and a 25% (F18) hexanal: organic acid product were included as positive controls. Formulations were added to test tube at concentration of 0.1%, 0.05%, 0.01% and 0.005%. Solutions were vortexed for 10 seconds to uniformly mix the solution. There were three replicate tubes per treatment. A suspension of *Salmonella typhimurium* ($10^4$ cfu/ml) was added to three test tubes containing the different dilution of each formulation. The solutions were vortexed, incubated at room temperature for 24 hours and then plated on XLT-4 agar for 48 hours before counting *Salmonella* colonies.

The effectiveness of each formulation as percent reduction compared to the control value is shown in the following tables.

TABLE 9

Effect of Butyraldehyde, Hexenal and Pelargonic Acid on *Salmonella*

| FORMULAS | F18 | X-1 | 65 | 66 | 67 | 68 | 69 | 70 | 71 | 72 | 73 | 74 |
|---|---|---|---|---|---|---|---|---|---|---|---|---|
| Pelargonic acid | 5 | 10 | 5 | 5 | 5 | 5 | 5 | 10 | 10 | 10 | 10 | 10 |
| Acetic acid (56%) | 20 | 20 | 20 | 20 | 20 | 20 | 25 | 15 | 15 | 15 | 15 | 20 |
| 2-hexenal | 25 | 20 | 20 | 15 | 10 | 5 | 0 | 20 | 15 | 10 | 5 | 0 |
| Propionic acid | 50 | 50 | 50 | 50 | 50 | 50 | 50 | 50 | 50 | 50 | 50 | 50 |
| Butyraldehyde | | | 5 | 10 | 15 | 20 | 20 | 5 | 10 | 15 | 20 | 20 |
| | 100 | 100 | 100 | 100 | 100 | 100 | 100 | 100 | 100 | 100 | 100 | 100 |

% Reduction of *Salmonella* Growth

| Concentration | F18 | X-1 | 65 | 66 | 67 | 68 | 69 | 70 | 71 | 72 | 73 | 74 |
|---|---|---|---|---|---|---|---|---|---|---|---|---|
| 0.005% | 26.7 | 21.2 | 26.7 | 9.1 | 4.2 | 0 | 0 | 9.1 | 15.2 | 1.2 | 0 | 0 |
| 0.01% | 70.9 | 52.1 | 44.8 | 40.0 | 11.5 | 0 | 0 | 67.3 | 38.2 | 6.7 | 0 | 0 |
| 0.05% | 100 | 100 | 100 | 100 | 94.5 | 69.7 | 0 | 100 | 99.4 | 95.2 | 77.0 | 0 |

TABLE 10

Effect of Citral, Hexenal and Pelargonic Acid on *Salmonella*

| FORMULAS | F18 | X-1 | 75 | 76 | 77 | 78 | 79 | 80 | 81 | 82 | 83 | 84 |
|---|---|---|---|---|---|---|---|---|---|---|---|---|
| Pelargonic acid | 5 | 10 | 5 | 5 | 5 | 5 | 5 | 10 | 10 | 10 | 10 | 10 |
| Acetic acid (56%) | 20 | 20 | 20 | 20 | 20 | 20 | 25 | 15 | 15 | 15 | 15 | 20 |
| 2-hexenal | 25 | 20 | 20 | 15 | 10 | 5 | 0 | 20 | 15 | 10 | 5 | 0 |
| Propionic acid | 50 | 50 | 50 | 50 | 50 | 50 | 50 | 50 | 50 | 50 | 50 | 50 |
| citral | 0 | 0 | 5 | 10 | 15 | 20 | 20 | 5 | 10 | 15 | 20 | 20 |
| | 100 | 100 | 100 | 100 | 100 | 100 | 100 | 100 | 100 | 100 | 100 | 100 |

% Reduction of *Salmonella* Growth

| Concentration | F18 | X-1 | 75 | 76 | 77 | 78 | 79 | 80 | 81 | 82 | 83 | 84 |
|---|---|---|---|---|---|---|---|---|---|---|---|---|
| 0.005% | 26.7 | 21.2 | 23.6 | 33.9 | 44.8 | 43.0 | 29.1 | 19.4 | 45.5 | 36.4 | 37.0 | 38.2 |
| 0.01% | 70.9 | 52.1 | 70.3 | 63.0 | 63.0 | 77.0 | 33.3 | 68.5 | 60.6 | 60.6 | 53.3 | 30.9 |
| 0.05% | 100 | 100 | 100 | 100 | 100 | 100 | 90.9 | 100 | 100 | 100 | 100 | 94.5 |

TABLE 11

Effect of Undecylenic, Hexenal and Pelargonic Acid on *Salmonella*

| FORMULAS | F18 | X-1 | 95 | 96 | 97 | 98 | 99 | 100 | 101 | 102 | 103 | 104 |
|---|---|---|---|---|---|---|---|---|---|---|---|---|
| Pelargonic acid | 5 | 10 | 5 | 5 | 5 | 5 | 5 | 10 | 10 | 10 | 10 | 10 |
| Acetic acid (56%) | 20 | 20 | 20 | 20 | 20 | 20 | 25 | 15 | 15 | 15 | 15 | 20 |
| 2-hexenal | 25 | 20 | 20 | 15 | 10 | 5 | 0 | 20 | 15 | 10 | 5 | 0 |
| Propionic acid | 50 | 50 | 50 | 50 | 50 | 50 | 50 | 50 | 50 | 50 | 50 | 50 |
| undecylenic | 0 | 0 | 5 | 10 | 15 | 20 | 20 | 5 | 10 | 15 | 20 | 20 |
|  | 100 | 100 | 100 | 100 | 100 | 100 | 100 | 100 | 100 | 100 | 100 | 100 |

% Reduction of *Salmonella* Growth

| Concentration | F18 | X-1 | F95 | F96 | F97 | F98 | F99 | F100 | F101 | F102 | F103 | F104 |
|---|---|---|---|---|---|---|---|---|---|---|---|---|
| 0.005% | 0 | 0 | 5.9 | 20.1 | 29.6 | 47.2 | 85.1 | 16.1 | 14.7 | 21.5 | 50.6 | 29.6 |
| 0.01% | 38.4 | 19.5 | 60.7 | 52.6 | 74.3 | 79.7 | 90.5 | 49.2 | 69.5 | 41.1 | 51.9 | 62.1 |
| 0.05% | 100 | 100 | 99.3 | 100 | 100 | 100 | 98.6 | 100 | 100 | 100 | 99.3 | 89.8 |

TABLE 12

Effect of Decadienal, Hexenal and Pelargonic Acid on *Salmonella*

| FORMULAS | F18 | X-1 | 85 | 86 | 87 | 88 | 89 | 90 | 91 | 92 | 93 | 94 |
|---|---|---|---|---|---|---|---|---|---|---|---|---|
| Pelargonic acid | 5 | 10 | 5 | 5 | 5 | 5 | 5 | 10 | 10 | 10 | 10 | 10 |
| Acetic acid (56%) | 20 | 20 | 20 | 20 | 20 | 20 | 25 | 15 | 15 | 15 | 15 | 20 |
| 2-hexenal | 25 | 20 | 20 | 15 | 10 | 5 | 0 | 20 | 15 | 10 | 5 | 0 |
| Propionic acid | 50 | 50 | 50 | 50 | 50 | 50 | 50 | 50 | 50 | 50 | 50 | 50 |
| 2,4 decadieneal | 0 | 0 | 5 | 10 | 15 | 20 | 20 | 5 | 10 | 15 | 20 | 20 |
|  | 100 | 100 | 100 | 100 | 100 | 100 | 100 | 100 | 100 | 100 | 100 | 100 |

% Reduction of *Salmonella* Growth

| Concentration | F18 | X-1 | 85 | 86 | 87 | 88 | 89 | 90 | 91 | 92 | 93 | 94 |
|---|---|---|---|---|---|---|---|---|---|---|---|---|
| 0.005% | 0 | 0 | 74.3 | 72.9 | 83.1 | 70.2 | 79.7 | 49.2 | 81.7 | 87.8 | 90.5 | 93.9 |
| 0.01% | 38.4 | 19.5 | 98.0 | 94.6 | 93.2 | 92.6 | 96.6 | 91.9 | 99.3 | 98.6 | 99.3 | 91.2 |
| 0.05% | 100 | 100 | 100 | 100 | 100 | 100 | 100 | 100 | 100 | 100 | 100 | 100 |

TABLE 13

Effect of Cinnamaldehyde, Hexenal and Pelargonic Acid on *Salmonella*

| FORMULAS | F18 | X-1 | 105 | 106 | 107 | 108 | 109 | 110 | 111 | 112 | 113 | 114 |
|---|---|---|---|---|---|---|---|---|---|---|---|---|
| Pelargonic acid | 5 | 10 | 5 | 10 | 5 | 5 | 5 | 10 | 10 | 10 | 10 | 10 |
| Acetic acid (56%) | 20 | 20 | 20 | 20 | 20 | 20 | 25 | 15 | 15 | 15 | 15 | 20 |
| 2-hexenal | 25 | 20 | 20 | 15 | 10 | 5 | 0 | 20 | 15 | 10 | 5 | 0 |
| Propionic acid | 50 | 50 | 50 | 50 | 50 | 50 | 50 | 50 | 50 | 50 | 50 | 50 |
| cinnamaldehyde | 0 | 0 | 5 | 10 | 15 | 20 | 20 | 5 | 10 | 15 | 20 | 20 |
|  | 100 | 100 | 100 | 100 | 100 | 100 | 100 | 100 | 100 | 100 | 100 | 100 |

% Reduction of *Salmonella* Growth

| Concentration | F18 | X1 | F105 | F106 | F107 | F108 | F109 | F110 | F111 | F112 | F113 | F114 |
|---|---|---|---|---|---|---|---|---|---|---|---|---|
| 0.005% | 50.3 | 29.9 | 31.0 | 39.9 | 26.8 | 5.9 | 21.6 | 31.5 | 24.7 | 22.6 | 37.8 | 23.1 |
| 0.01% | 73.3 | 50.3 | 59.2 | 62.9 | 44.6 | 45.6 | 18.4 | 66.0 | 55.6 | 57.1 | 45.6 | 15.3 |
| 0.05% | 100 | 100 | 100 | 100 | 100 | 100 | 84.8 | 100 | 100 | 100 | 100 | 90.6 |

TABLE 14

Effect of Decanal, Hexenal and Pelargonic Acid on *Salmonella*

| FORMULAS | F18 | X-1 | 115 | 116 | 117 | 118 | 119 | 120 | 121 | 122 | 123 | 124 |
|---|---|---|---|---|---|---|---|---|---|---|---|---|
| Pelargonic acid | 5 | 10 | 5 | 10 | 5 | 5 | 5 | 10 | 10 | 10 | 10 | 10 |
| Acetic acid (56%) | 20 | 20 | 20 | 20 | 20 | 20 | 25 | 15 | 15 | 15 | 15 | 20 |
| 2-hexenal | 25 | 20 | 20 | 15 | 10 | 5 | 0 | 20 | 15 | 10 | 5 | 0 |
| Propionic acid | 50 | 50 | 50 | 50 | 50 | 50 | 50 | 50 | 50 | 50 | 50 | 50 |

TABLE 14-continued

| decanal | 0 | 0 | 5 | 10 | 15 | 20 | 20 | 5 | 10 | 15 | 20 | 20 |
|---|---|---|---|---|---|---|---|---|---|---|---|---|
| | 100 | 100 | 100 | 100 | 100 | 100 | 100 | 100 | 100 | 100 | 100 | 100 |

| | % Reduction of *Salmonella* Growth | | | | | | | | | | | |
|---|---|---|---|---|---|---|---|---|---|---|---|---|
| Concentration | F18 | X1 | F115 | F116 | F117 | F118 | F119 | F120 | F121 | F122 | F123 | F124 |
| 0.005% | 50.3 | 29.9 | 39.9 | 47.2 | 56.6 | 77.5 | 88.5 | 51.9 | 45.1 | 70.7 | 92.7 | 91.6 |
| 0.01% | 73.3 | 50.3 | 61.8 | 89.0 | 93.7 | 94.2 | 94.8 | 67.6 | 74.4 | 86.9 | 93.2 | 94.8 |
| 0.05% | 100 | 100 | 100 | 100 | 100 | 100 | 97.4 | 100 | 100 | 100 | 100 | 97.4 |

TABLE 15

Effect of Furfural, Hexenal and Pelargonic Acid on *Salmonella*

| FORMULAS | F18 | X-1 | 125 | 126 | 127 | 128 | 129 | 130 | 131 | 132 | 133 | 134 |
|---|---|---|---|---|---|---|---|---|---|---|---|---|
| Pelargonic acid | 5 | 10 | 5 | 10 | 5 | 5 | 5 | 10 | 10 | 10 | 10 | 10 |
| Acetic acid (56%) | 20 | 20 | 20 | 20 | 20 | 20 | 25 | 15 | 15 | 15 | 15 | 20 |
| 2-hexenal | 25 | 20 | 20 | 15 | 10 | 5 | 0 | 20 | 15 | 10 | 5 | 0 |
| Propionic acid | 50 | 50 | 50 | 50 | 50 | 50 | 50 | 50 | 50 | 50 | 50 | 50 |
| furfural | 0 | 0 | 5 | 10 | 15 | 20 | 20 | 5 | 10 | 15 | 20 | 20 |
| | 100 | 100 | 100 | 100 | 100 | 100 | 100 | 100 | 100 | 100 | 100 | 100 |

| | % Reduction of *Salmonella* Growth | | | | | | | | | | | |
|---|---|---|---|---|---|---|---|---|---|---|---|---|
| Concentration | F18 | X1 | F125 | F126 | F127 | F128 | F129 | F130 | F131 | F132 | F133 | F134 |
| 0.005% | 50.3 | 29.9 | 33.6 | 40.4 | 41.4 | 34.1 | 41.4 | 28.9 | 29.9 | 39.3 | 24.7 | 47.7 |
| 0.01% | 73.3 | 50.3 | 63.4 | 43.5 | 33.6 | 34.1 | 36.7 | 78.6 | 41.4 | 33.1 | 29.9 | 28.9 |
| 0.05% | 100 | 100 | 100 | 97.9 | 95.8 | 81.7 | 0 | 100 | 100 | 90.6 | 80.1 | 6.4 |

Results:
1. At 5% pelargonic acid, butyraldehyde by itself is not as effective as trans-2-hexenal.
2. At 10% pelargonic acid, 20% butyraldehyde was as effective as 20% trans-2-hexenal.
3. At both, 5% and 10% pelargonic acid, butyraldehyde can partially replace trans-2-hexenal.
4. At 5% pelargonic acid, citral by itself is not as effective as trans-2-hexenal.
5. At 10% pelargonic acid, 20% citral was as effective as 20% trans-2-hexenal.
6. At both, 5% and 10% pelargonic acid, citral can partially replace trans-2-hexenal.
7. At both, 5% and 10% pelargonic acid, undecylenic aldehyde can replace trans-2-hexenal.
8. At both, 5% and 10% pelargonic acid, decadienal aldehyde can replace trans-2-hexenal.
9. At both, 5% and 10% pelargonic acid, cinnamaldehyde can replace trans-2-hexenal.
10. At both, 5% and 10% pelargonic acid, decanal can replace trans-2-hexenal.
11. At both, 5% and 10% pelargonic acid, furfural can replace trans-2-hexenal.
12. All the formulations tested were as effective and in some instance better than a positive formula with 25% or 20% trans-2-hexenal or the formic/propionic formulation.

CONCLUSION

Pelargonic acid potentiates the efficacy of each individual aldehyde and aldehyde combination. It will be apparent to those skilled in the art that variations and modifications of the invention can be made without departing from the sprit and scope of the teachings above. It is intended that the specification and examples be considered as exemplary only and are not restrictive.

The invention claimed is:
1. An antimicrobial composition for extending the shelf-life of water, feed or feed ingredients, comprising:
   water,
   5-15 wt. % of pelargonic acid,
   10-20 wt. % of acetic acid,
   40-50 wt. % of propionic acid,
   5-30 wt. % of trans-2-hexenal, and
   5-30 wt. % of a $C_1$-$C_{24}$ aldehyde selected from the group consisting of, cinnamaldehyde, undecylenic aldehyde, butyraldehyde, 2,4 decadienal, and decanal.
2. A method for extending the shelf-life of water, feed or feed ingredients, comprising:
   spray-treating or admixing to water, feed or feed ingredients, an effective amount of a composition comprising:
   water,
   5-15 wt. % of pelargonic acid,
   10-20 wt. % of acetic acid,
   40-50 wt. % of propionic acid,
   5-30 wt. % of trans-2-hexenal, and
   5-30 wt. % of a $C_1$-$C_{24}$ aldehyde selected from the group consisting of, cinnamaldehyde, undecylenic aldehyde, butyraldehyde, 2,4 decadienal, and decanal.
3. The method of claim 2, wherein the composition is provided in an amount that is effective against bacteria, viruses, mycoplasmas or fungi present in drinking water, feed and feed ingredients.
4. The method of claim 2, wherein the composition is spray-treated or admixed to feed or feed ingredients at a rate of 0.25 to 2 kilograms per ton of feed or feed ingredients.

* * * * *